US 6,629,057 B2

(12) United States Patent
Zweig et al.

(10) Patent No.: US 6,629,057 B2
(45) Date of Patent: *Sep. 30, 2003

(54) COMPREHENSIVE VERIFICATION SYSTEMS AND METHODS FOR ANALYZER-READ CLINICAL ASSAYS

(75) Inventors: Stephen E. Zweig, Los Gatos, CA (US); Thomas D. Downey, Cupertino, CA (US); Benjamin J. Spink, Stanford, CA (US); Benjamin G. Meyer, Saratoga, CA (US)

(73) Assignee: Beckman Coulter, Inc., Fullerton, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/435,253

(22) Filed: Nov. 5, 1999

(65) Prior Publication Data

US 2003/0139903 A1 Jul. 24, 2003

(51) Int. Cl.[7] .................. G06F 11/30; G06F 15/00; G21C 17/00
(52) U.S. Cl. .................. 702/182; 73/73; 374/102
(58) Field of Search ............... 702/22, 27, 85, 702/89, 108, 81, 116, 131, 130, 136, 183, 30–32, 182, 188; 374/100–106; 356/36, 39–42; 73/29, 73; 436/164, 172, 174, 37

(56) References Cited

U.S. PATENT DOCUMENTS

| 4,523,852 A | 6/1985 | Bauer | 356/421 |
|---|---|---|---|
| 4,849,340 A | 7/1989 | Oberhardt | 435/13 |
| 5,418,143 A | 5/1995 | Zweig | 435/13 |
| 5,504,011 A | 4/1996 | Gavin et al. | 436/69 |
| 5,591,403 A | 1/1997 | Gavin et al. | 422/73 |
| 5,757,666 A | * 5/1998 | Schreiber et al. | 702/22 |
| 5,872,713 A | * 2/1999 | Douglas et al. | 702/85 |
| 5,997,927 A | * 12/1999 | Gics | 426/383 |
| 6,061,128 A | * 5/2000 | Zweig et al. | 356/243.4 |
| 6,103,351 A | * 8/2000 | Ram et al. | 428/195 |

OTHER PUBLICATIONS

Accumetrics, Ultegra Rapid Platelet Function Assay–TRAP, http://www.accumetrics.com/prodinfo/ultegra2.htm, Nov. 1, 2001.*

* cited by examiner

Primary Examiner—Marc S. Hoff
Assistant Examiner—Mary Catherine Baran
(74) Attorney, Agent, or Firm—William H. May; D. David Hill

(57) ABSTRACT

The present invention provides improved systems and methods for verifying accurate test performance of monitoring systems, particularly for point-of-care service. Such monitoring systems typically include a test element containing the test reagent(s), and an electronic analyzer device. A blood or other patient sample is applied to the test element, which is introduced to the analyzer. As the reaction proceeds, the analyzer stores the data and outputs the testing result. Accuracy in the result is dependent upon proper functioning of both the test element and the analyzer. The systems of the present invention provide indicators to evaluate the integrity of the test elements and a verification device to evaluate the performance of the analyzer. Such systems may be provided as kits with instructions for use.

23 Claims, 4 Drawing Sheets

COMPREHENSIVE VERIFICATION SYSTEMS AND METHODS FOR ANALYZER-READ CLINICAL ASSAYS

CROSS-REFERENCES TO RELATED APPLICATIONS

The disclosure of the present application is related to that of application Ser. No. 09/138,824, the full disclosure of which is incorporated herein by reference.

BACKGROUND OF THE INVENTION

Monitoring of blood samples for clinical indicators, such as glucose levels, cholesterol levels and coagulation times, is medically imperative to properly treat patients undergoing drug therapy and to safeguard the health of patients with chronic conditions. For example, such monitoring is used with oral anticoagulant therapy. Oral anticoagulants are used to treat patients with a trial fibrillation, deep vein thrombosis (DVT), artificial heart valves, post-myocardial infarction and other cardiovascular disorders. These medications prevent blood clots which can cause thromboembolic events, such as stroke, recurrent myocardial infarction and pulmonary embolism. However, oral anticoagulant drug actions are highly variable requiring individualized management of each patient's treatment. The most common method of managing such treatment is by using a prothrombin time test. Here, a blood sample is taken and is subject to a reagent, thromboplastin, which initiates the clotting cascade. The time in which the blood takes to clot is measured by an analytical machine.

Traditionally, such testing was undertaken in centralized laboratories, where typically one or more full time medical technologists administered to various types of automated analytical machines. However, as technology has advanced, it has become both feasible and medically necessary to take certain tests out of the centralized clinical laboratory and into the hands of patients and physicians. Some tests, such as blood glucose, must be performed so frequently (several times a day) as to make centralized testing impractical for most diabetics. Other tests, such as the prothrombin time testing, must also be performed at a high frequency (optimally weekly) and utilize samples that tend to deteriorate rapidly, over several hours and thus are less suited for centralized laboratories.

Therefore, simple, reliable, point-of-care tests have been developed. A blood sample is taken, often obtained by finger stick methods, and placed on a disposable test element (test strip) containing the test reagents, usually stored in a dry form on the test element. The test element is then analyzed by a small, portable electronic analyzer device (meter) which outputs the testing result. To ensure that the testing result is accurate, the analyzer system (meter plus reagent) must undergo routine quality control (QC) testing. Erroneous testing results may be due to reagent degradation, instrument failure, mechanical or electrical malfunction or operator misuse.

In centralized laboratories, such QC testing is typically undertaken on a daily basis by using "liquid controls". These controls consist of samples of one or more analytes with known values. If the analytical machine or the reagents malfunction, for whatever reason, the liquid controls will have an unexpected value. This result will inform the manufacturer or operator that there is a problem, however it will not reveal the underlying failure mode for the system.

Although daily liquid QC testing is quite appropriate for full time professionals in labs that test many patients, it can triple the cost and time per test in the point-of-care environment. This can raise the barrier of such testing so high that the tests are not used, even when they are needed. In addition, many point-of-care systems use disposable, one-time-use test elements containing dry reagents. Because such dry-reagent tests are unitized, daily liquid QC tells the user only that the disposable unit just tested was good. It does not guarantee that the next unitized test will be good.

Due to the limitations in QC testing, patient use of monitoring systems has been significantly impeded. Home prothrombin time tests, such as the Roche-Boehringer Coaguchek, became available for use in America in 1997. However, the adoption of such tests was slowed because of the requirement that each patient perform two levels of liquid QC testing each time the test was used, compounding the time and cost of each test. But the highest cost is to the health of the patient. Patients denied access to prothrombin time tests, due to burdensome liquid QC requirements, may not receive proper anticoagulation treatment. For example, a recent US government patient outcomes research (PORT) study estimated that for a trial fibrillation alone, 40,000 excess strokes per year occurred due to sub-optimal anticoagulation treatment. Patients suffering from a trial fibrillation have a 4.3% chance of having a stroke each year. Warfarin, an oral anticoagulant, can reduce the incidence of stroke in these patients by 83%. However, numerous studies have shown that warfarin has a narrow therapeutic range. Too little warfarin is ineffective and too much can cause bleeding. Thus, monitoring by frequent prothrombin time tests is imperative. And, the results of such monitoring must be accurate. Thus, there is a need for improved methods of quality assurance testing.

SUMMARY OF THE INVENTION

The present invention provides improved systems and methods for verifying accurate test performance of monitoring systems, particularly for point-of-care service. Such monitoring systems typically include a test element containing the test reagent(s), and an electronic analyzer device. A blood or other patient sample is applied to the test element, which is introduced to the analyzer. As the reaction proceeds, the analyzer stores the data and outputs the testing result. Accuracy in the result is dependent upon proper functioning of both the test element and the analyzer. The systems of the present invention provide indicators to evaluate the integrity of the test elements and a verification device to evaluate the performance of the analyzer. Such systems may be provided as kits with instructions for use.

The method of the present invention tests both for proper status and functioning of the test element and of the electronic system without destruction or consumption of any of the system components or reagents. Most disposable, test elements are comprised of dry reagents. Such dry reagent test elements are usually made in the factory in high volumes, and are subjected to a high degree of statistical quality control. The test elements are developed to have a known shelf life and are individually unit packed in sealed foil containers. Assuming that the test elements are competently manufactured, which is addressed by normal medical GMP regulations and systems, the predominant failure modes of the test elements are exposure to environmental degradation factors during shipping and storing. Specifically, the reagents comprising the test elements may suffer degradation by exposure to excess humidity or temperature leading to testing malfunction. To confirm that environmental degradation has not occurred, indicators are provided. Such indicators include, but are not limited to, a moisture indicator and/or a time-temperature indicator.

Each testing element may be packaged with its own drying agent packet which serves as a moisture indicator. Typically, the drying agent is a desiccant which changes color when it has reached capacity. The desiccant may be blue in its initial state. An increase in humidity causes the desiccant to absorb the extra moisture. At which point the desiccant is replete, the hue changes to another color, such as pink. Such a color change indicates that the testing element has been exposed to excess humidity and the dry reagent(s) may not function properly. Such use of indicating desiccants is fairly common in the diagnostics industry.

The testing elements may be further packaged with a time-temperature indicator (TTI). The characteristics of the TTI are designed to match the time-temperature stability characteristics of the degradable material, in this case the test element, as closely as possible within a conservative margin. The TTI progressively changes state over time as a function of temperature. Thus, the TTI will reveal if the package has been exposed to extreme temperature conditions during shipping and storage. A variety of different TTIs are currently used in other industries to ensure safe shipping and storage practices. For example, TTIs are used to determine the shelf-life of temperature sensitive foods, such as perishable dairy products and produce, and to ensure that vaccines retain potency after shipment and storage.

A number of different TTIs currently exist, and they can be produced by a number of different methods. TTIs can be integrating or non-integrating. Non-integrating TTIs are used to determine if the indicator has been transiently exposed to an abnormally high or low temperature. Integrating TTIs preserve a running history of temperature by an integrating element. Either type may be used with the test elements of the present invention, however integrating TTIs are typically preferable as they more closely mimic the actual stability characteristics of such degradable test elements.

A variety of different approaches can be devised to create an integrating TTI. An integrating TTI is most useful when it exactly matches the stability characteristics of the product it is monitoring. For highest fidelity, a low-cost microprocessor-temperature sensor method may be employed. With this unit, the microprocessor will periodically poll the state of the temperature sensor. The results can then be stored in memory, where they can be used in a number of different ways. In one scheme, the microprocessor stores a "maximum life" number representing the sum of the series of time-temperature readings that are allowed. The microprocessor is then programmed to periodically poll the state of the temperature sensor, compare the results to a look-up table or algorithm, and then subtract the output from the look-up table or algorithm from the maximum life number. Typically, for a temperature sensitive product, the look-up table or algorithm will be designated to output a larger number at higher temperatures than at lower temperatures. When the "maximum life" reaches zero, the electronic integrating TTI can indicate end of life by, for example, changing a liquid crystal display from a "+" to a "−". Other electronic integrating TTI schemes are also possible.

Although microprocessor methods may give the highest accuracy, such methods may not be cost effective. An alternative lower cost TTI is a chemical colorimetric indicator. In this case, the colorimetric indicator may be fixed to the side panel of the shipping box of degradable test elements, or to each individually foil packed test element. Appearing with the indicator may be an associated reference chart. Exposure of the box to excessive temperatures over a period of time may be revealed by the production of a color on the indicator. This color may then be matched to a specific range on the reference chart. The reference chart will describe if the test element has been exposed to excess temperature for too long a period of time. If this is the case, the user knows that the test elements should not be used.

In some configurations, it may be advantageous to affix the time-temperature indicator, and optionally a moisture indicator, directly to the test element. This may allow more accurate assessment of the degradation of each individual test element. In addition, such location of the environmental degradation indicators directly on the test element may allow the indicators to be automatically scanned by the analyzer upon insertion of the test element. This may be accomplished by attaching such means to the analyzer, typically photo-optical such as an array of photodetectors or the like, to automatically scan the indicators at the time at which the test element is inserted. This would automatically verify the status of the environmental degradation indicators without further human intervention. Such automatic scan mechanisms have the advantage of continuously verifying, without relying in the attention of the human operator. Similarly, a feature may be incorporated in the analyzer in which a signal of a degraded test element will interrupt function of the analyzer. This will eliminate the possibility of erroneous results being generated from degraded test elements.

In addition to checking the test element, the method of the present invention verifies proper functioning of the analyzer. This is accomplished with the use of electronic verification or "control" devices or circuits. Such verification devices, previously disclosed in U.S. application Ser. No. 09/138, 824, can simulate an underlying chemical reaction observed by the analyzer, e.g., the action of an enzymatic sample interacting with a disposable reagent. Thus, when a verification device is inserted into or incorporated as part of an analyzer, signals are generated which mimic reactions that would be generated by reacting reagents on a real test element. If the analytical device returns the proper result after analysis of the verification device, then the proper functioning of the analytical device has been verified. Consequently, verification of the analyzer may accomplished independently of the test element. This both avoids destruction of the one-time-use test element and limits all testing variables to the analyzer. Certain modifications to this practice also fall within the scope of the invention. For example, the electronic verification device may be built into the analyzer, and the analytical device verified without the need for a manual insertion step. Moreover, the analyzer may automatically test both the functioning of the analyzer (for example, each time the device is turned on and/or between successive tests) and the adequacy of each testing element to provide a very high level of assurance that each test is accurate and that the system has not failed.

The combined use of such electronic and environmental verification devices is also superior to using liquid controls. Electronic verification devices are inherently more precise. This is because liquid controls must have ranges set to accommodate a large number of different analyzers in the field, each running a large number of different batches of reagents. Consequently, the control range must be fairly large, usually ±30%. By contrast, it is possible to control the deviations in electronic verification device performance to a much tighter level, usually ±20% or less. Thus, electronic verification devices are more sensitive to aberrantly performing analyzers. Similarly, time-temperature indicators can be selected to be sensitive enough to detect reagent degradation at a fairly early stage, typically when reagents have changed their performance by less than ±10%. Thus, reliance on the absence of environmental degradation is warranted when the test element reagent chemistry has known stability characteristics, and when the test element is virtually certain to be functional when leaving the manufacturing facility.

In addition to test element and analyzer failure modes, a number of additional failure modes occur due to user errors. Because these user errors often occur on a random basis, neither test element indicators, electronic verification devices nor liquid controls are particularly effective at detecting this type of error. The best way to detect random user-errors is to build a large number of internal self checks into the analyzer which operate each time a test is run. These checks may include but are not limited to checking for sufficient sample volume, checking for proper temperature control throughout the reaction, checking for abnormal reaction chemistry, checking for microprocessor code and data integrity, checking for obscured optical path, etc. These self-tests are an effective way of detecting user errors that might otherwise be missed by other verification means.

Although daily liquid QC is traditional for clinical laboratories, risk-benefit analysis suggests that this is not always appropriate in all situations. Alternative, more cost-effective methods are possible that can detect errors and malfunctions with equal or greater efficiency. The present invention provides such improved systems and methods for verifying accurate test performance of monitoring systems, particularly for point-of-care service. The systems of the present invention provide essentially complete verification means using established technology that has proven successful as individual indicators of specific conditions. Together, these indicators and verification means provide a simple, cost-effective method of user QC testing of monitoring devices.

DESCRIPTION OF THE SPECIFIC EMBODIMENTS

The present invention provides improved systems and methods for verifying accurate test performance of monitoring systems. The methods are particularly useful for point-of-care service. While the description is directed particularly at coagulation testing, it will be appreciated that the invention applies to all monitoring of clinical indicators, including glucose levels, cholesterol levels and the like.

Figure 1:
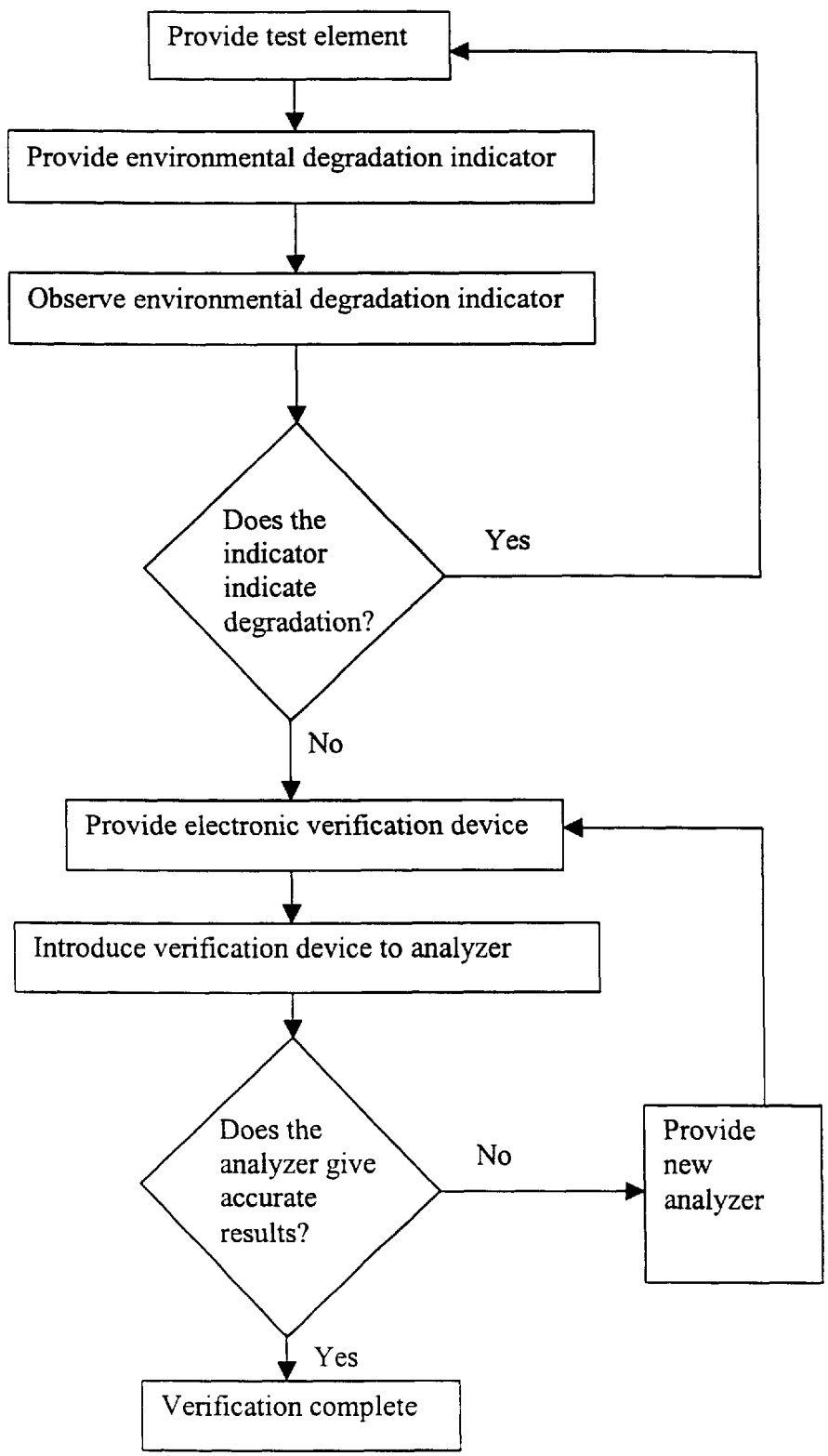
FIG. 1 is a flowchart illustrating the verification method.

The method of the present invention is set forth in FIG. 1. This method provides a simple and easy series of steps in which the end-user of a portable monitoring system may perform QC testing. Such testing provides complete evaluation of the monitoring system, identifying possible malfunction due to a variety of causes, such as degradation of the test element reagents, electrical or mechanical malfunction of the analyzer, and user error. Previously, such complete evaluation required the use of more costly and less accurate methods, such as the use of liquid controls.

Figure 2:
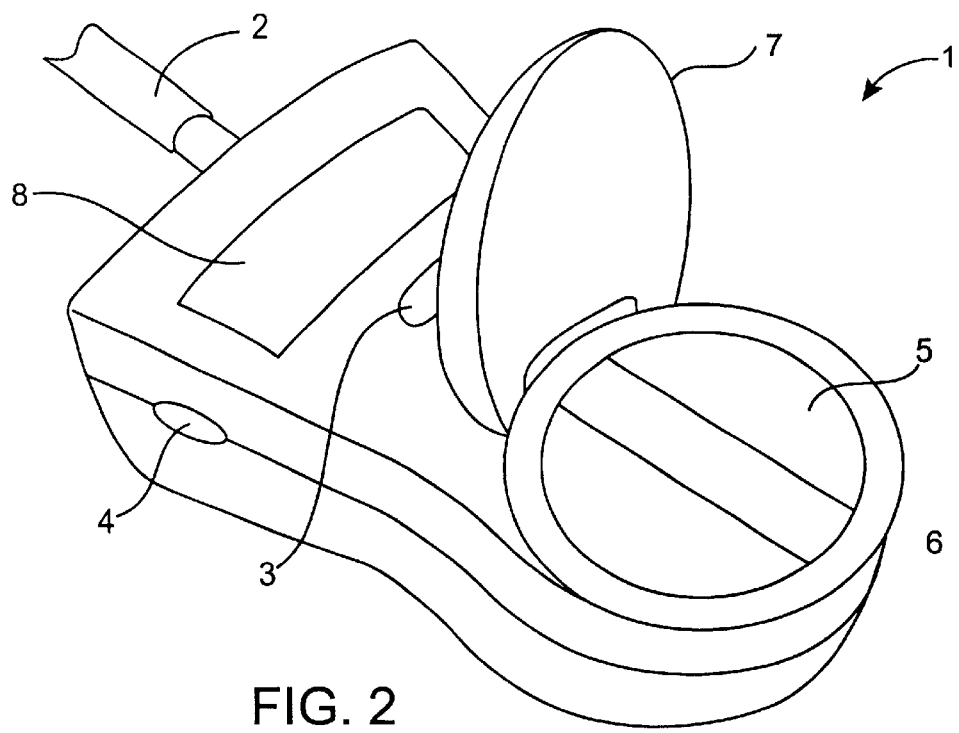
FIG. 2 is a perspective view of an electronic analyzer embodiment.

The improved systems of the present invention include a series of components to verify accurate performance of the monitoring system. In the case of coagulation testing, an analyzer is used to evaluate the clotting time of a blood sample. FIG. 2 depicts the basic features of a small, portable electronic analyzer 1 for point-of-care use. The analyzer 1 is powered by an AC power adapter port and cord 2 and a power button 3 on the face of analyzer. Calibration may be performed with the use of the side calibration button 4. The test element is mounted on the circular holder 5 over the optics block 6, to allow for analysis of the sample. A lid 7 is provided to protect the sample during testing, and the test result is shown on the display 8.

Figure 3:
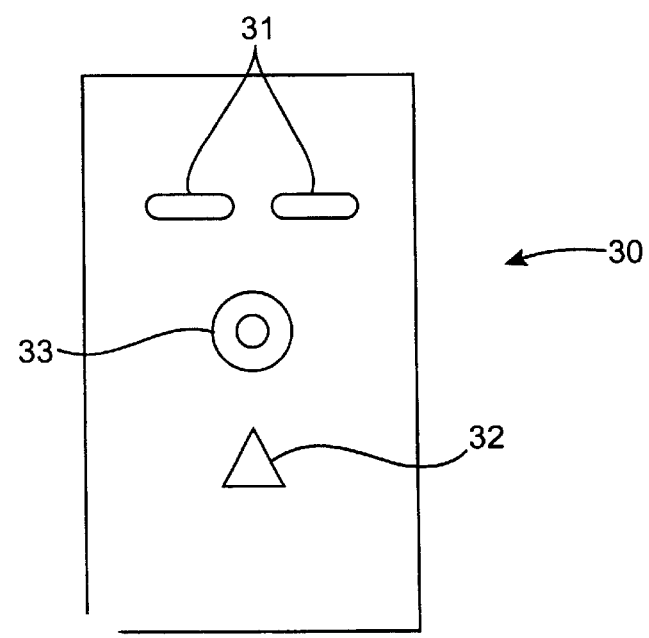
FIG. 3 is a top view of a test element embodiment.

FIG. 3 shows a preferred embodiment of the test element 30. Two oval windows 31 are used for positioning in the analyzer 1. The triangle 32 points to the circular target area 33. The target area 33 is where the blood sample is applied.

Figure 4:
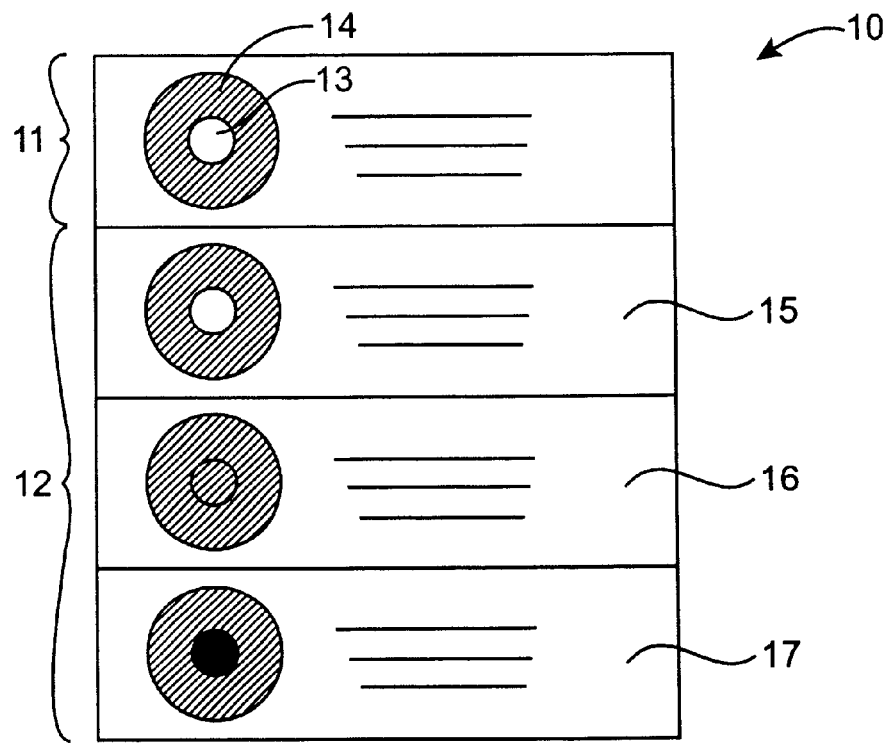
FIG. 4 illustrates a time-temperature indicator embodiment.

Test elements 30 to be used with the electronic analyzer 1 are packaged in boxes for shipping and storing. On the side panel of each box is an environmental degradation indicator. In a preferred embodiment, the environmental degradation indicator is a time-temperature indicator 10 (HEATmarker™, Lifelines Technology Inc., Morris Plains, N.J.), as depicted in FIG. 4. The time-temperature indicator 10 is comprised of a calorimetric indicator 11 and an associated reference chart 12. The calorimetric indicator 11 should exhibit a marked contrast between the inner ring 13 and the outer ring 14. The inner ring 13 should be a lighter color than the outer ring 14, as shown in the first tier 15 of the reference chart 12. If the inner ring 13 has changed color and matches the outer ring 14, as shown in the second tier 16, or is darker than the color of the outer ring 14, as shown in the third tier 17, then the test elements 30 have been exposed to excessive temperatures for a prolonged period of time. In such a case, the test elements 30 should not be used.

Figure 5:
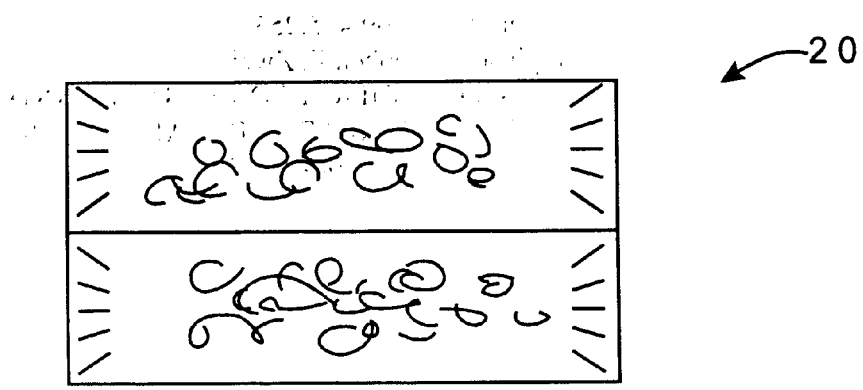
FIG. 5 illustrates a moisture indicator embodiment.

Each test element 30 is individually unit packed in sealed foil containers. Each unit is typically labeled with the lot number, expiration date, CAL Codes (calibration codes), and storage instructions. Within each foil container is an additional environmental degradation indicator. In a preferred embodiment, the environmental degradation indicator is a moisture indicator 20, as depicted in FIG. 5. The moisture indicator 20 is comprised of a desiccant which changes color with moisture. The moisture indicator 20 should be blue; if it is pink, the test element 30 has been exposed to too much humidity. In such a case, the test element 30 should not be used.

Figure 6:
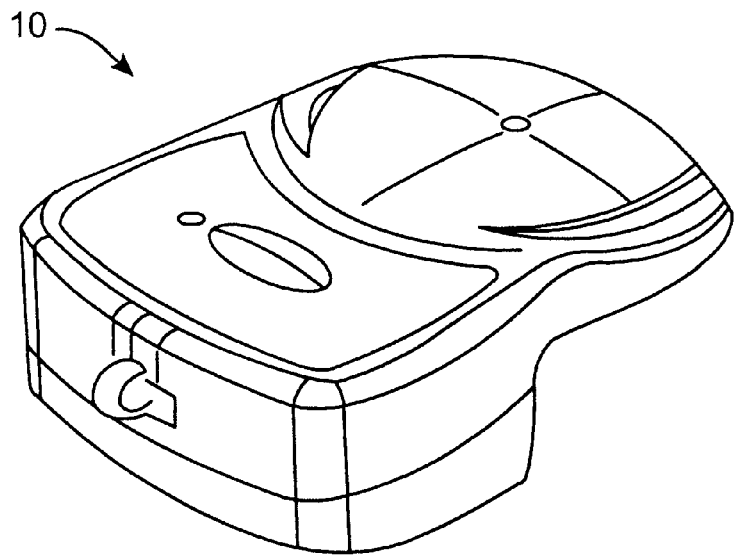
FIG. 6 is a perspective view of an electronic verification device.
Figure 7:
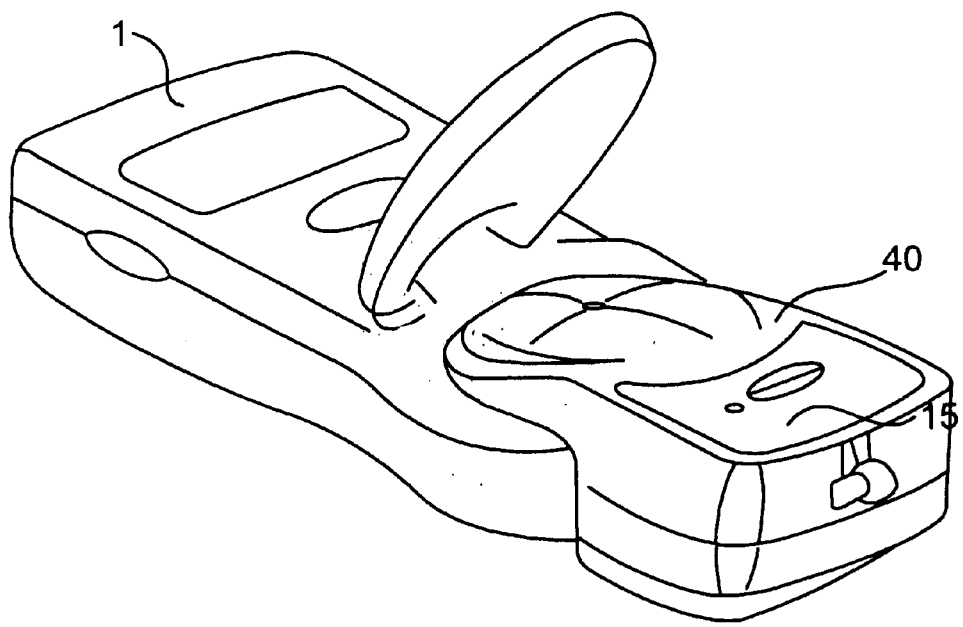
FIG. 7 is a perspective view of an electronic verification device docking with an electronic analyzer.

In addition to verifying that the test element 30 has not degraded due to environmental conditions, the analyzer 1 is also verified for proper functioning. This is accomplished with the use of an electronic verification device. The construction and operation of such verification devices are described in detail in copending U.S. application Ser. No. 09/138,824, the full disclosure of which has previously incorporated by reference. A preferred embodiment of an electronic verification device 40 is depicted in FIG. 6. When a verification device 40 is inserted into an analyzer 1, as shown in FIG. 7, signals are generated which mimic reactions that would be generated by reacting reagents on a real test element. If the analyzer 1 returns the proper result after interrogating the verification device 40, then the proper functioning of the analyzer 1 has been verified.

The systems and methods of the present invention provide complete verification means using established technology that has proven successful as individual indicators of specific conditions. Together, these indicators and verification means provide a simple, cost-effective method of user QC testing of monitoring devices.

What is claimed is:

1. A method for verifying accurate performance of an analyzer system which electronically interrogates a chemical test element, said method comprising:

providing a test element with an environmental degradation indicator;
observing the environmental degradation indicator to confirm that the test element has not degraded; and
confirming correct operation of the analyzer based on interrogation of a verification device by the analyzer;
wherein accurate performance of both the analyzer and the test element of the analyzer system is found based on non-degradation of the test element and accurate operation of the analyzer.

2. A method as in claim 1, further comprising:
providing an electronic verification device configured to be introduced to the analyzer and to test and/or calibrate the analyzer; and
introducing the verification device into the analyzer.

3. A method as in claim 1, wherein the verification device is incorporated into the analyzer.

4. A method as in claim 1, wherein the observing step comprises the analyzer interrogating the environmental degradation indicator.

5. A method as in claim 1, wherein the observing step comprises a user visually observing the environmental degradation indicator.

6. A method as in claim 1, wherein the environmental degradation indicator is a time-temperature indicator.

7. An electronic analyzer device which receives and electronically interrogates a chemical test element comprising:
means to automatically assess the state of an environmental degradation indicator associated with the chemical test element; and
means to electronically verify the proper function of the electronic analyzer device,
whereby accurate performance of both the analyzer device and the test element is found based on non-degradation of the test element and accurate operation of the analyze.

8. A method for verifying accurate performance of an analyzer system which electronically interrogates a chemical test element, said method comprising:
providing an electronic verification device configured to be introduced to the analyzer and to test and/or calibrate the analyzer;
introducing the verification device into the analyzer;
confirming correct operation of the analyzer based on interrogation of the verification device by the analyzer;
providing a test element with an environmental degradation indicator;
introducing the test element with the degradation indicator into the analyzer;
observing response from analyzer to confirm that the test element has not degraded;
wherein accurate performance of both the analyzer and the test element of the analyzer system is found based on non-degradation of the test element and accurate operation of the analyzer.

9. A kit for use with an electronic analyzer system comprising:
(i) a first container comprising a chemical test element, wherein said first container has a first environmental degradation indicator;
(ii) a second container comprising said first container with the chemical test element, wherein said second container has a second environmental degradation indicator; and
(iii) instructions for use setting forth verifying performance of the analyzer system which electronically interrogates the test element; and confirming correct operation of the analyzer based on interrogation of a verification device by the analyzer; wherein accurate performance of both the analyzer and the test element of the analyzer system is found based on non-degradation of the test element and accurate operation of the analyzer.

10. The kit of claim 9, further comprising:
providing an electronic verification device configured to be introduced to the analyzer and to test and/or calibrate the analyzer; and
introducing the verification device into the analyzer.

11. The kit of claim 10, wherein the chemical test element produces a calorimetric, fluorescent, or luminescent signal when a sample is applied, wherein the electronic verification device mimics such a signal.

12. The kit of claim 9, wherein the verification device is incorporated into the analyzer.

13. The kit of claim 9, wherein the observing step comprises a user visually observing the first and second environmental degradation indicators.

14. The kit of claim 9, wherein the first container is a sealed foil container for individually packing the test element; and Wherein the second container is a box for shipping or storing at least one sealed foil container comprising said test element.

15. The kit of claim 9, wherein the first environmental degradation indicator is a moisture indicator; and wherein the second environmental degradation indicator is a time-temperature indicator.

16. The kit of claim 9, wherein the chemical test element comprises a dry substrate.

17. A kit for use with an electronic analyzer system comprising:
(i) a chemical test element having an environmental degradation indicator, wherein the indicator is affixed to the chemical test element; and
(ii) instructions for use setting forth the following method for verifying performance of the analyzer system which electronically interrogates the test element:
observing the environmental degradation indicator to confirm that the test element has not degraded; and
confirming correct operation of the analyzer based on interrogation of a verification device by the analyzer; wherein accurate performance of both the analyzer and the test element of the analyzer system is found based on non-degradation of the test element and accurate operation of the analyzer.

18. The kit of claim 17, further comprising:
providing an electronic verification device configured to be introduced to the analyzer and to test and/or calibrate the analyzer; and
introducing the verification device into the analyzer.

19. The kit of claim 18, wherein the chemical test element produces a calorimetric, fluorescent, or luminescent signal when a sample is applied, wherein the electronic verification device mimics such a signal.

20. The kit of claim 17, wherein the verification device is incorporated into the analyzer.

21. The kit of claim 17, wherein the observing step comprises the analyzer interrogating the environmental degradation indicator.

22. The kit of claim 17, wherein the environmental degradation indicator is a time-temperature indicator.

23. The kit of claim 17, wherein the chemical test element comprises a dry substrate.

* * * * *